US010789461B1

(12) United States Patent
Agrawal et al.

(10) Patent No.: US 10,789,461 B1
(45) Date of Patent: Sep. 29, 2020

(54) AUTOMATED SYSTEMS AND METHODS FOR TEXTUAL EXTRACTION OF RELEVANT DATA ELEMENTS FROM AN ELECTRONIC CLINICAL DOCUMENT

(71) Applicant: INNOVACCER INC., San Francisco, CA (US)

(72) Inventors: Vibhuti Agrawal, Delhi (IN); Gourav Sanjukta Bhabesh, Baripada (IN)

(73) Assignee: INNOVACCER INC., San Francisco, CA (US)

( * ) Notice: Subject to any disclaimer, the term of this patent is extended or adjusted under 35 U.S.C. 154(b) by 0 days.

(21) Appl. No.: 16/743,175

(22) Filed: Jan. 15, 2020

(30) Foreign Application Priority Data

Oct. 24, 2019 (IN) .............................. 201921043365

(51) Int. Cl.
| | |
|---|---|
| *G06F 17/27* | (2006.01) |
| *G06K 9/00* | (2006.01) |
| *G06F 40/205* | (2020.01) |
| *G16H 10/60* | (2018.01) |

(52) U.S. Cl.
CPC ....... *G06K 9/00463* (2013.01); *G06F 40/205* (2020.01); *G06K 9/00469* (2013.01); *G16H 10/60* (2018.01)

(58) Field of Classification Search
CPC ..................................................... G06F 17/27
USPC .... 704/9, 235, 500; 707/779, 723, 722, 741, 707/625, 610; 705/4, 29; 715/234, 780; 700/96; 713/189
See application file for complete search history.

(56) References Cited

U.S. PATENT DOCUMENTS

| | | | |
|---|---|---|---|
| 6,408,294 B1 | 6/2002 | Getchius | ........... G06F 16/24534 |
| 6,484,161 B1 | 11/2002 | Chipalkatti | ............ G06Q 30/02 |
| 7,047,242 B1 | 5/2006 | Ponte | ..................... G06Q 10/00 |
| 7,611,466 B2 * | 11/2009 | Chalana | ............... A61B 8/0858 |
| | | | 382/128 |
| 8,849,693 B1 | 9/2014 | Koyfman | ............... G06Q 30/02 |
| 8,977,953 B1 | 3/2015 | Pierre | ................... G06F 40/284 |

(Continued)

FOREIGN PATENT DOCUMENTS

| | | | | |
|---|---|---|---|---|
| WO | WO 2018/057647 | 3/2018 | ............... | C12Q 1/68 |
| WO | WO 2018/166853 | 9/2018 | ............ | G16H 10/60 |

OTHER PUBLICATIONS

U.S. Appl. No. 16/363,897, filed Mar. 25, 2019.

(Continued)

*Primary Examiner* — Michael Colucci
(74) *Attorney, Agent, or Firm* — Hayes Soloway P.C.

(57) ABSTRACT

A system and method for extracting relevant data elements from a file for conversion to a tabular format includes a computing device receiving an XML format file having a loop with nested blocks. Each of the blocks has at least one data element. Features are extracted from each data element. These extracted features are processed using a machine learning algorithm to estimate a column header value for the data elements relative to a data schema. With the data element classified, a configuration file is generated to map the column header value to the data elements of the XML file. The configuration file is used to extract the data elements from the XML file to a tabular format. In the healthcare industry, the system and method may be used to extract relevant health information from a clinical document for conversion to a tabular format.

20 Claims, 6 Drawing Sheets

(56) References Cited

U.S. PATENT DOCUMENTS

| | | | |
|---|---|---|---|
| 9,542,393 B2 | 1/2017 | Morton | G06F 16/7844 |
| 9,727,591 B1 | 8/2017 | Sharma | G06F 16/215 |
| 10,056,078 B1 | 8/2018 | Shepherd | G06F 16/632 |
| 10,147,504 B1 | 12/2018 | Stettin et al. | G16H 50/30 |
| 2003/0018633 A1 | 1/2003 | Horn | G06F 17/18 |
| 2004/0215629 A1 | 10/2004 | Dettinger | G06F 16/2452 |
| 2005/0065956 A1* | 3/2005 | Brown | G06F 16/252 |
| 2005/0107902 A1* | 5/2005 | Blouin | G06Q 10/087 700/96 |
| 2005/0119534 A1 | 6/2005 | Trost | G06F 19/00 |
| 2005/0131778 A1* | 6/2005 | Bennett | G06Q 10/0875 705/29 |
| 2006/0041539 A1* | 2/2006 | Matchett | G06Q 10/0639 |
| 2006/0075001 A1* | 4/2006 | Canning | G06F 8/65 |
| 2007/0239724 A1 | 10/2007 | Ramer | G06F 16/951 |
| 2009/0313232 A1* | 12/2009 | Tinsley | H04N 21/25883 |
| 2010/0121879 A1* | 5/2010 | Greenberg | G06F 16/248 707/779 |
| 2010/0199169 A1* | 8/2010 | Gnech | G06F 16/972 715/234 |
| 2010/0287162 A1 | 11/2010 | Shirwadkar | G06F 16/3338 |
| 2012/0253793 A1 | 10/2012 | Ghannam | G06F 17/27 |
| 2013/0197936 A1 | 8/2013 | Willich | G06Q 50/22 |
| 2014/0006061 A1* | 1/2014 | Watanabe | G06Q 40/08 705/4 |
| 2014/0149446 A1 | 5/2014 | Kuchmann-Beauger | G06F 17/30389 |
| 2014/0188835 A1 | 7/2014 | Zhang | G06F 17/2705 |
| 2014/0344261 A1* | 11/2014 | Navta | G06F 16/951 707/723 |
| 2015/0164430 A1 | 6/2015 | Hu | A61B 5/7264 |
| 2015/0363478 A1* | 12/2015 | Haynes | G06F 16/26 707/625 |
| 2016/0098387 A1 | 4/2016 | Bruno | G06F 17/27 |
| 2016/0162473 A1 | 6/2016 | Cogley | G06F 40/51 |
| 2016/0371453 A1 | 12/2016 | Bowman | G06F 19/00 |
| 2016/0373456 A1 | 12/2016 | Vermeulen | G06F 16/25 |
| 2017/0091162 A1* | 3/2017 | Emanuel | G06F 40/169 |
| 2017/0102693 A1 | 4/2017 | Kidd | G05B 19/41865 |
| 2017/0161372 A1 | 6/2017 | Fernandez | G06F 16/35 |
| 2017/0199928 A1 | 7/2017 | Zhao | G06F 16/24578 |
| 2017/0256173 A1 | 9/2017 | Burford | G09B 5/125 |
| 2017/0344646 A1 | 11/2017 | Antonopoulos | H04L 9/008 |
| 2017/0371881 A1* | 12/2017 | Reynolds | G06F 16/256 |
| 2018/0052842 A1 | 2/2018 | Hewavitharana et al. | G06F 17/3043 |
| 2018/0158146 A1 | 6/2018 | Turner | G06Q 40/02 |
| 2018/0225320 A1 | 8/2018 | Saini | G06F 16/215 |
| 2018/0232443 A1 | 8/2018 | Delgo | G06Q 30/06 |
| 2018/0367557 A1 | 12/2018 | Brown | H04L 63/1425 |
| 2019/0012390 A1 | 1/2019 | Nishant | G06N 20/00 |
| 2019/0050445 A1* | 2/2019 | Griffith | G06F 16/213 |
| 2019/0156198 A1 | 5/2019 | Mars | G06N 20/20 |
| 2019/0179820 A1 | 6/2019 | El Kaed | G06F 16/2471 |
| 2019/0180757 A1 | 6/2019 | Kothari | G10L 17/005 |
| 2019/0324964 A1 | 10/2019 | Shiran | G06N 20/00 |
| 2020/0004749 A1* | 1/2020 | Slezak | G06F 16/2282 |

OTHER PUBLICATIONS

U.S. Appl. No. 16/387,016, filed Apr. 17, 2019.

Office Action issued in U.S. Appl. No. 16/387,016, dated Jun. 25, 2019 (11 pgs).

Office Action issued in U.S. Appl. No. 16/387,016, dated Oct. 17, 2019 (17 pgs).

Office Action issued in U.S. Appl. No. 16/363,897, dated Sep. 9, 2019 (38 pgs).

Morid et al. "Supervised Learning Methods for Predicting Healthcare Costs: Systematic Literature Review and Empirical Evaluation", 2018, AMIA Annu Symp Proc. pp. 1312-1321.

Wang et al. "Detecting Transportation Modes Based on LightBGM Classifier from GPS Trajectory Data", 2018 26$^{th}$ International Conference on Geoinformatics, Kunming, 2018, pp. 1-7.

Zhang et al. "Health reform and out-of-pocket payments: lessens from China", Health Policy and Planning, vol. 29, Issue 2, Mar. 2014, pp. 217-226, https://doi.org/10.1093/heapol/czt006.

Iyengar et al. "A Trusted Healthcare Data Analytics Cloud Platform", 2018 IEEE 38$^{th}$ International Conference on Distributed Computing Systems (ICDCS), Vienna, 2018, pp. 1238-1249.

U.S. Appl. No. 16/363,897, filed Mar. 25, 2019, Bhabesh et al.

U.S. Appl. No. 16/387,016, filed Apr. 17, 2019, Hasija et al.

Notice of Allowance issued in U.S. Appl. No. 16/387,016, dated Feb. 10, 2020 (14 pgs).

Office Action issued in U.S. Appl. No. 16/363,897, dated Feb. 26, 2020 (36 pgs).

International Search Report and Written Opinion issued in PCT/US20/13802 dated Mar. 25, 2020 (10 pgs).

International Search Report and Written Opinion issued in PCT/US20/16827 dated Apr. 22, 2020 (7 pgs).

* cited by examiner

FIG. 2

AUTOMATED SYSTEMS AND METHODS FOR TEXTUAL EXTRACTION OF RELEVANT DATA ELEMENTS FROM AN ELECTRONIC CLINICAL DOCUMENT

CROSS REFERENCE TO RELATED APPLICATION

This application claims benefit of Indian Application Serial No. 201921043365, filed Oct. 24, 2019, the entire disclosure of which is incorporated herein by reference.

FIELD OF THE DISCLOSURE

The present disclosure is generally related to electronic data processing and more particularly is related to automated systems and methods for textual extraction of relevant data elements from an electronic clinical document.

BACKGROUND OF THE DISCLOSURE

The Affordable Care Act of 2010 was a pivotal point in the U.S. healthcare industry for numerous reasons, one of which is that it gave access to individuals and organizations with Information Technology (IT) domain expertise to healthcare industry data. This digital transformation of healthcare industry data in the U.S. generated a tremendous amount of electronic data in the form of clinical and claims data. This massive volume of data creation, and the speed at which it is created, has brought the IT-sector together with the healthcare industry, ultimately giving rise to a new industry of health data analytics. Health data analytics has lead to the generation of new interventions for healthcare providers based on the insights drawn from the patient health information (PHI). The IT sector has large infrastructure to assimilate the data and it has capabilities to mine meaningful in-sights from the data, such that it is well situated to help the health providers leverage meaningful analytical insights from the healthcare industry data. However, there are challenges to implementing such a system.

One of the most crucial steps in this fusion of disparate sectors is the transmission of health data from the health exchanges to the data analytics team of the IT companies. Currently, this step is plagued with a problem rooted in the inherent nature of these industries. The health sector heavily depends on unstructured, textual format of data. In contrast, in the IT industry, all of the infrastructure and methodologies were and are built upon the assumption that incoming data will be structured and represented in the legacy format of tabular format, i.e., the form of rows and columns. Because the healthcare industry data is largely unstructured, the ingestion of this data by the IT industry becomes a problematic point for IT organizations. This mismatch has lead to heavy losses in terms of efficiency and accuracy of the data being ingested into the data warehouses of the IT industry. In turn, it has resulted in poor analysis of the health data, eventually leading to a potential loss of opportunity for health providers to come up with new and improved interventions for the patients.

One of the key elements of this healthcare industry data is its complexity in terms of both standardizations and structuredness. Most of the raw data generated at a granular level of a patient's healthcare journey is in the form of text, such as doctors' notes, clinical and lab test results, prescribing of drugs, among others. All this raw data is in the form of text which must be converted into relevant codes, and then arranged in a particular structured format. In the field of data terminology, this healthcare industry data is called the electronic health record (EHR). The EHR, in spite of being partially standardized, has a substantial drawback-when the digitization of the health information started taking place, it brought about the creation of many sources of the standardization of the health data, resulting in numerous variations and duplications of the same data. These variations and duplications in the data resulted in misinformation, errors in classification of data, processing errors, and inefficiencies within the analytical data field.

Some of the most recognized standards codes across the health industry include: ICD (International Classification of Diseases), a medical classification list by the World Health Organization; LONIC (Logical Observation Identifiers Names and Codes) which is a database and universal standard for identifying medical laboratory observations; RxNorm, which contains codes for all medications available on the US market, and is used in personal health records applications; and SNOMED (Systematized Nomenclature of Medicine) which is a systematically organized computer processable collection of medical terms providing codes, terms, synonyms and definitions used in clinical documentation and reporting.

Some of the formats used in structuring the EHR include C-CDA (Consolidated Clinical Document Architecture) which is an Extensible Markup Language (XML)-based markup standard intended to specify the encoding, structure, and semantics of clinical documents for exchange; HL7 (Health Level Seven) which provides a comprehensive framework and related standards for the exchange, integration, sharing, and retrieval of electronic health information that supports clinical practice and the management, delivery and evaluation of health services; and FHIR (Fast Healthcare Interoperability Resources), a draft standard describing data formats and elements (resources) and an application programming interface (API) for exchanging electronic health records.

One of the most widely used formats used in writing EHR is the C-CDA, which is essentially an XML document which can be used to specify the encoding, structure, and semantics of clinical documents for exchange. XML is a text-based markup language that defines a set of rules for encoding documents in a format that can be read and comprehended by both humans and machines. While XML has emerged as a new standard for intelligent document management and electronic publishing, there are substantial challenges in the ability to read XML files in an automated manner.

While XML represents structured data, to a degree, there is no single format that all XML files follow. This is problematic, in part, because it makes it difficult to parse all the XML files with one standard parser. This problem of requiring different parsers for different XML files is further intensified for large and complex XML documents, which is common in EHR, wherein the users don't know the structure or the contents of the files. To add to the list of negative issues with XML data, XML files may contain multiple standards of codes, as discussed above, which can be in any one of LOINC, ICD, or SNOMED formats. This further aggravates the problem of parsing XML documents.

In general terms, the C-CDA document has become a lock and key system in the industry, where the key can be understood as a parser or a very specific set of instructions to decode documents within the EHR. Often the standards are openly available, yet the C-CDA document still needs human intervention to setup the parser. This leads to delays in data ingestion for the efficient analysis of the EHR documents and adds expense and inaccuracies to the overall process.

Additionally, another important aspect of healthcare analytics is maintaining the security of the PHI and other related data. Due to the sensitive nature of the PHI, any exposure to an unauthorized entity can have severe consequences, as it is a strict requirement of the Health Insurance Portability and Accountability Act (HIPAA) and other, similar laws to maintain patient confidentiality. With the transmission and communication of the PHI between the healthcare sector and the IT industry, the risk of a breach in confidentiality increases as a patient's health data increases.

Thus, a heretofore unaddressed need exists in the industry to address the aforementioned deficiencies and inadequacies.

SUMMARY OF THE DISCLOSURE

Embodiments of the present disclosure provide a system and method for the extraction of relevant data elements from an electronic file for conversion to a tabular format. Briefly described, in architecture, one embodiment of the system, among others, can be implemented as follows. A computing device receives an Extensible Markup Language (XML) format file, the XML file having at least one loop with nested blocks, wherein each of the nested blocks has at least one data element. A processor of the computing device executes instructions for: extracting features from the data elements; processing the extracted features using a machine learning algorithm to estimate a column header value for the data elements relative to a data schema; classifying the data elements from the XML file using the extracted features; and generating a configuration file which maps the column header value to the data elements of the XML file. A tabular format file is generated by parsing the XML file using the configuration file generated by processor to convert the data elements from the XML file to a tabular format.

The present disclosure can also be viewed as providing methods for extracting relevant data elements from an electronic file for conversion to tabular format. In this regard, one embodiment of such a method, among others, can be broadly summarized by the following steps: receiving, in a computing device, an Extensible Markup Language (XML) format file, the XML file having at least one loop with nested blocks, wherein each of the nested blocks has at least one data element; extracting features from the data elements; processing, with a processor of the computing device, the extracted features using a machine learning algorithm to estimate a column header value for the data elements relative to a data schema; classifying the data elements from the XML file using the extracted features; generating a configuration file which maps the column header value to the data elements of the XML file; and parsing the XML file using the configuration file to convert the data elements from the XML file to a tabular format.

The present disclosure can also be viewed as providing a system for extracting relevant health information from a clinical document in an Extensible Markup Language (XML) format for conversion to a tabular format. Briefly described, in architecture, one embodiment of the system, among others, can be implemented as follows. A first computing device receives the clinical document, wherein the clinical document has nested loops with a plurality of attributes describing data elements, wherein the plurality of data elements correspond to health information within the clinical document. A processor of the first computing device executes instructions for: extracting features from at least one of the plurality of attributes or the data elements of a clinical document using textual analysis; processing the extracted features using a machine learning algorithm to estimate a column header value for the data elements relative to a predefined data schema; extracting features from at least one of the plurality of attributes or the data elements using textual analysis; classifying the data elements from the clinical document using the extracted features; and generating a configuration file which maps the column header value to the data elements of the clinical document using a key-value pair, where the key of the key-value pair provides a column header value name from a data-lake schema and a value from the key-value pair provides an XPath to the data element of the clinical document. At least one second computing device is in communication with the first computing device, wherein, at least in one second computing device, the configuration file is used to convert the data elements from the clinical document to a tabular format.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 is a partial image of C-CDA document having an XML format, used with the system for the extraction of relevant data elements from an electronic file for conversion to a tabular format, in accordance with the first exemplary embodiment of the present disclosure.

DETAILED DESCRIPTION

Figure 1:
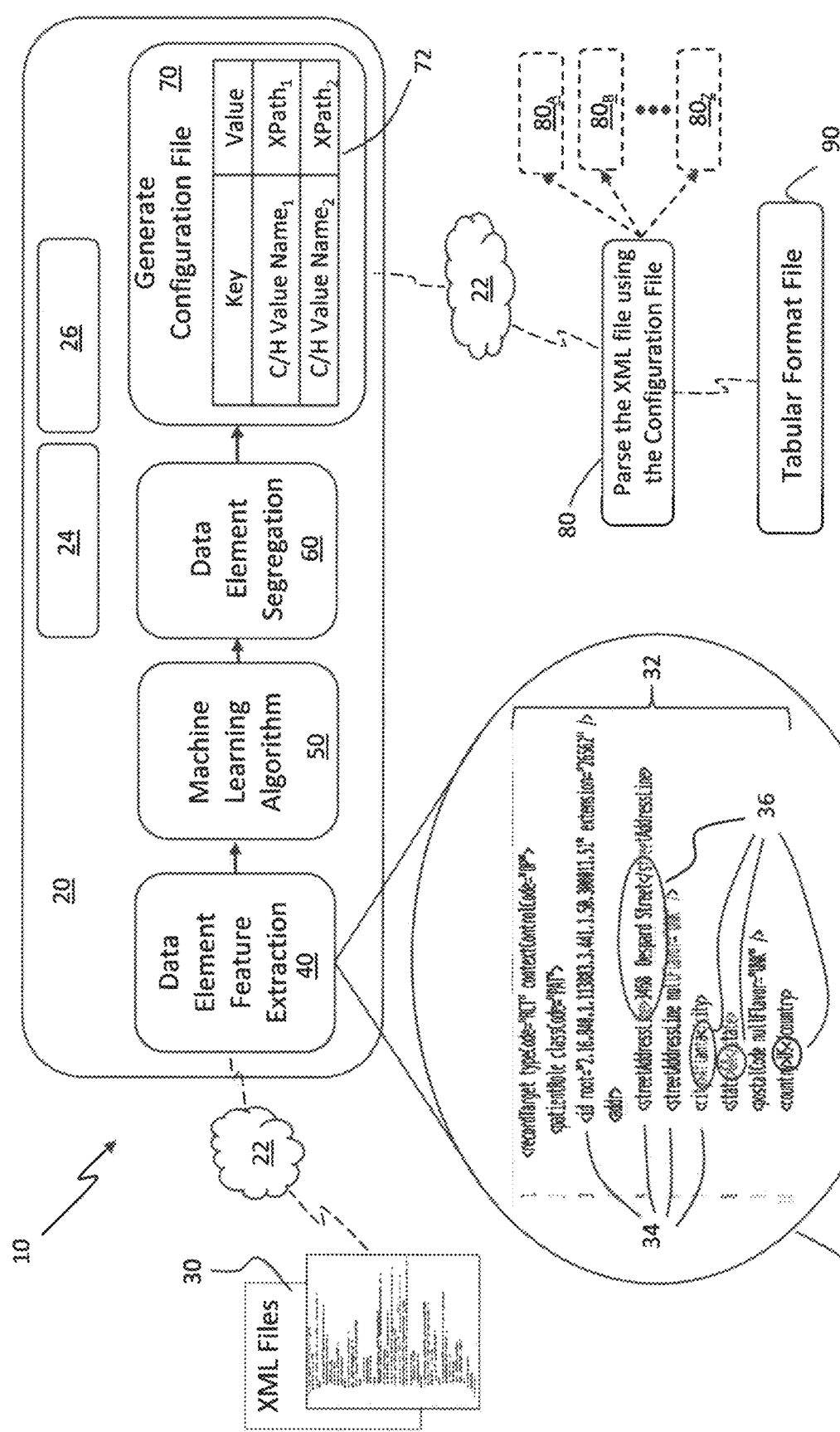
FIG. 1 is a diagrammatic illustration of a system for the extraction of relevant data elements from an electronic file for conversion to a tabular format, in accordance with a first exemplary embodiment of the present disclosure.

To address the shortcomings described in the Background, novel methods and systems have been developed to ensure the integrity, efficiency and accuracy of healthcare analytics. In particular, these novel methods and systems may provide substantial benefits with the extraction of health data from the clinical document, which is widely used by the health information exchanges to transmit PHI related to the clinical facet of the patient's journey, and conversion of that health data into an IT-usable tabular format. As previously discussed, the effectiveness of the health analytics industry is plagued by the problem of efficiently and accurately ingesting health data from unstructured or semi-structured formats to a structured, tabular format. Health data, and specifically the clinical data, needs to be parsed to extract the relevant data such that it can be ingested by the IT organization in the form of tabular data. However, parsing of the unstructured or semi-structured data found within a clinical document is often one of the most difficult tasks.

The subject disclosure uses machine learning algorithmic processing to provide solutions to these types of unconventional problems in data extraction and conversion, i.e., where there is not one single rule or key to parse certain files, but rather, a dynamic parsing system must be employed. One of the most powerful features of machine learning algorithms is its capability to explore the hidden patterns in data. In accordance with this disclosure, machine learning algorithms and other tools have been used to create a methodology to extract the relevant data elements from clinical documents in the healthcare field and map them to the columns headers used in the data schema of IT organizations. Since machine learning processing is not plagued by being too specific, it can be a great tool to generalize the extraction process of health data. While the clinical document widely used in the healthcare industry is not a free flowing text, it is generally unstructured or semi-structured, but with data customarily spread along specific patterns which may follow healthcare industry standards. Machine learning algorithms have proved to be a beneficial tool for capturing these patterns.

The present disclosure helps in generalizing the parser methodology, thereby increasing efficiency in terms of time to ingest data, accuracy of labelling a data point to a particular column header, and decrease the chances of losing the data from the health document. The increasing number of health documents and fast adaptation of digitizing the health data has led to numerous number of standards populating in the health industry which needs a smart parser to analyze and understand all these kinds of information, such that they can be parsed into data lakes used within the IT industry. Using the machine learning algorithms to find relevant patterns in the health data and parsing the data into required column header(s), and/or columns or headers, provides a substantial advantage to both the health providers and the patients in terms of better interventions and quick diagnosis.

While the system and methods of this disclosure may have utility within a variety of industries, for clarity, description is provided relative to use within the healthcare industry. Use of the disclosed system and methods herein within fields, industries, or settings beyond healthcare and with health data is considered within the scope of the present disclosure.

FIG. 1 is a diagrammatic illustration of a system for the extraction of relevant data elements from an electronic file for conversion to a tabular format 10, in accordance with a first exemplary embodiment of the present disclosure. The system for the extraction of relevant data elements from an electronic file for conversion to a tabular format 10, which may be referred to herein as 'system' 10 includes a computing device 20 receiving one or more Extensible Markup Language (XML) format files 30. The computing device 20 may receive the XML files 30 via an upload or feed using an electronic connection, such as a network connection 22, which may include any type of network communication protocol. The computing device 20 may be any type of computer, server, or other electronic, digital computing system, and it includes at least one processor 24 and at least one non-transitory memory 26, along with other possible computing components, such as a power supply, databases, applications and software, input/output devices, communication devices, or others.

While XML files 30 may include most any type of file having an XML format, the subject disclosure is particularly beneficial with clinical documents used in the healthcare industry. These clinical documents may include, for example, a C-CDA (Consolidated Clinical Document Architecture) file which has an XML format. Other examples of XML formatted clinical documents may also be used. The XML files 30 received by the computing device have at least one loop 32 with nested blocks 34, wherein each of the nested blocks 34 has at least one data element 36, as shown in the enlarged portion of an exemplary XML file 30 in FIG. 1, and as further described in more detail relative to FIG. 2.

The processor 24 of the computing device 20 is configured for executing instructions to perform functions. In general terms, these instructions include, at a minimum, extracting features from data element 36, as shown at block 40, processing each data element 36 with its extracted feature using a machine learning algorithm to estimate a column header value for the data elements 36 relative to a data schema, as shown at block 50. The data elements 36 are classified from the XML file 30 using the extracted features with the help of the machine learning algorithm 50, as shown at block 60. At block 70, a configuration file is generated which maps the column header value to the data elements 36 of the XML file 30. In broad terms, this processing is used to determine the relevant information from the XML file 30 using, in part, machine learning algorithms. Machine learning processing is a subset of artificial intelligence which utilizes algorithms and statistical models to perform analysis without using explicit instructions from a human elsewhere, relying on patterns and inference instead.

In the present disclosure, when an XML file 30, such as a C-CDA clinical document is uploaded to the computer system 20, it processes the XML file 30 and pin-points the location of each data element 36, or substantially all data elements 36, and assigns each data element 36 to a column in the final data schema. The output of the computing system 20 is effectively a dictionary which contains the name of the columns in the data schema as its key and path to the data element 36 in the XML file 30 as its value. This output is referred to as a configuration file. Using the configuration file, the XML file can be later parsed, at block 80, and then used or consumed by another system to extract the data from the XML file 30 such that it can be converted to a tabular format, as shown at block 90. For example, the system 10 reads the configuration file and extracts the data elements 36 from the C-CDA file and populates them into a table to be stored for further analysis to be performed. This parsing, formatting into a tabular file, and/or further analysis may be achieved in a second, separate computing system or it may occur within the computing system 20. For example, it may be advantageous for this portion of the processing to be scaled over many processors within many computing devices to provide the advantage of parallel computing to extract the data elements 36 quickly and efficiently, which is discussed in greater detail further within this description. Ultimately, the system 10 allows for the efficient and accurate extraction of relevant data elements 36 from the electronic XML file 30 for conversion of the data into a tabular format which is used within the IT industry.

Figure 2:
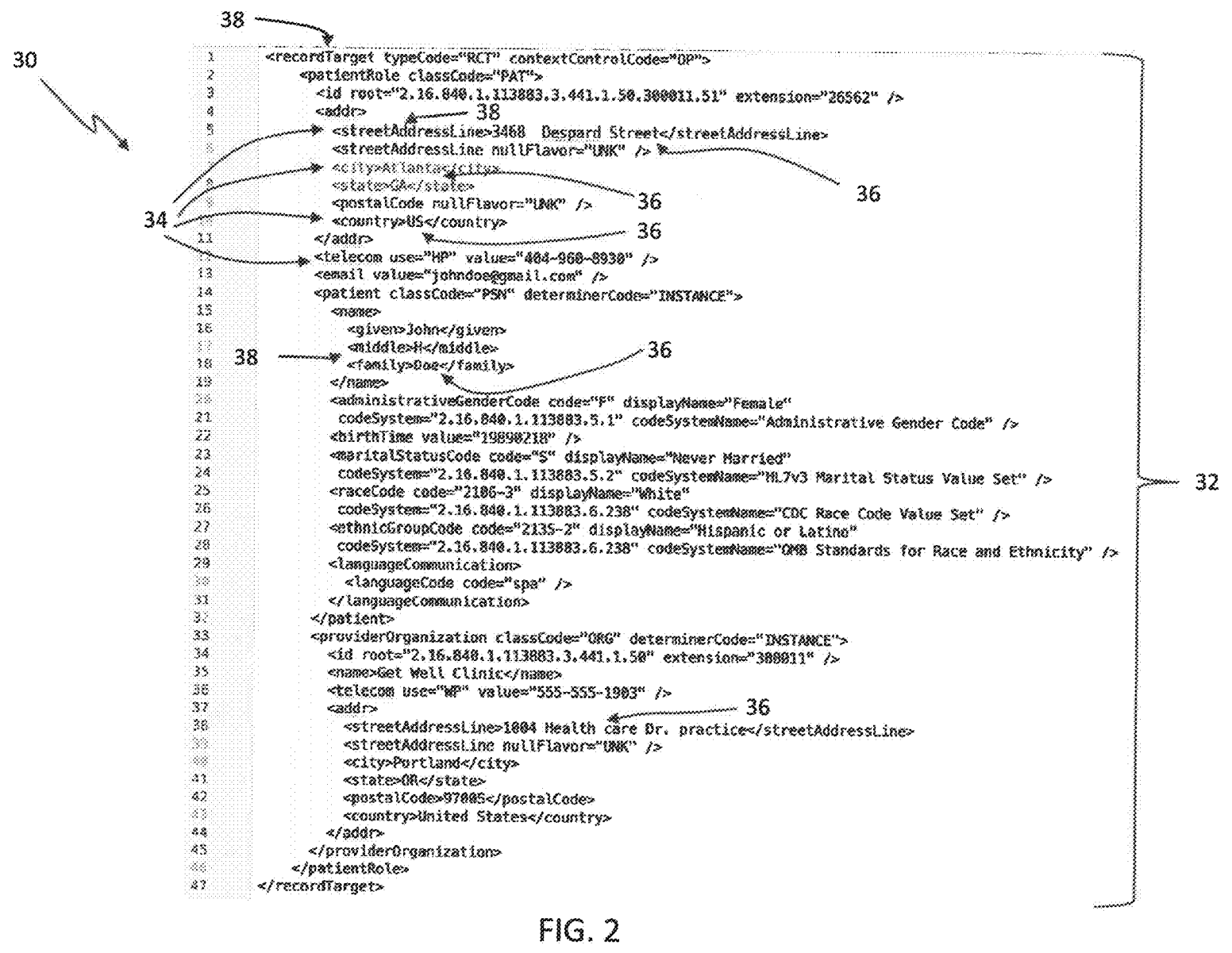

Further details of the subject disclosure are provided relative to FIGS. 2-5. With reference to FIG. 2 first, FIG. 2 is a partial image of C-CDA document having an XML format, used with the system for the extraction of relevant data elements from an electronic file for conversion to a tabular format 10, in accordance with the first exemplary embodiment of the present disclosure. In particular, FIG. 2 illustrates the different components that form a C-CDA document. As shown, the C-CDA document includes at least one nested loop 32, but it is very common for a C-CDA document to include many nested loops 32, each of which includes one or more attributes 38 describing one or more data elements 36 which are stored at the core of each loop 32. In the XML format of FIG. 2, the attributes 38 start with a forward angle bracket ("<") or are enclosed within the angle brackets ("< . . . >"). This is the format of XML data which is stored within the core of each loop 32.

The loops 32, or angle bracketed blocks, are generally constructed from nested blocks 34 or strings of text, each of which may contain one or more attributes 38 and/or one or more data elements 36. For example, the attribute 38 "recordTarget" defines a loop 32 consisting of information related to the patient's demographics. The loop 32 starts with an angled bracket at line 1 and ends at line 47, wherein the patient's demographics are contained between line 1 and line 47. Within this loop 32 are a number of blocks 34 which correlate to aspects of the patient's demographics, such as their street address at line 5, their address city at line 7, their address state at line 8, country at line 10, name at lines 16-18, etc. The blocks 34 can also be correlated to the patient's sex, marital state, race, ethnicity, language, or other aspects of the patient's demographics, as indicated at lines 20-31. Moreover, block 34 within a C-CDA can also be correlated to healthcare provider information, such as the provider name and address, as indicated from lines 33-45.

Within the block 34 are the attributes identified by the angled brackets, for example, "<recordTarget>" in line 1, "<streetAddressLine>" in line 5, etc., which correspond to, and describe, relevant data elements 36. The data elements 36 are characterized as the textual health data or other data which is specific to an individual patient. As can be seen, the data elements 36 for the patient are located proximate to the respective attributes 38. For example, the data element "3468 Despard Street" for the "<streetAddressLine>" or "GA" for "<state>". Some data elements are for an individual patient, such as a name, address, or birthdate, medical test results, etc., whereas other data elements 36 may correspond to the patient's other demographic attributes, such as sex, marital status, ethnicity, etc. Numerous other examples of data values 36 are shown in FIG. 2. It is noted that every data element 36, even the data elements 36 with minutest detail, will always be contained between the angled bracket block. For example, the data element 36 "3468 Despard Street" on line 5 is contained between "<streetAddressLine>" and "</streetAddressLine>" such that the value of that data element is correlated to the corresponding attribute 38.

The features are first extracted from these data elements, as shown in block 40, and then processing at block 50 employs a machine learning algorithm to read through each of the loops 32 and blocks 34 or lines while estimating a value of a data element. The estimated value may be the column header value, or column and/or header value, or another value in a specified data schema using the machine learning model which has been trained on the data set. In FIG. 2, a machine learning model was specifically trained on the demographics data, such that it can be used to differentiate between the various data elements 36 present inside the "recordTarget" loop 32. Other machine learning models may be used for other types of data, such as data containing medical information, test or lab results, diagnosis, pharmaceutical information, or other health-related data.

It is noted that the machine learning algorithm or model may be understood as a multi-classifier that classifies the given data elements 36 into respective column headers. The system 10 may have three such machine learning models that differentiate data elements 36 into their subgroups. The three models may be for demographic data, clinical data, and identifier elements. Demographics data may include all the data pertaining to the patients and the providers, including names, addresses, and other personal identifiable information. The clinical data may contain the parts of the C-CDA where there are sections having information about patient vitals, test or lab results, allergies, codes such as ICD, LOINC, SNOMED, RxNorm, immunization, insurance, family history, procedures, problems, medication history, and/or encounter history. The identifier model may help in ensuring that the correct model—of the demographics model and clinical model—is being used in identifying a given data element 36. All the three models may work in conjugation with one another to deliver a very accurate and fast prediction as to which column header the data element 36 belongs.

Figure 3:
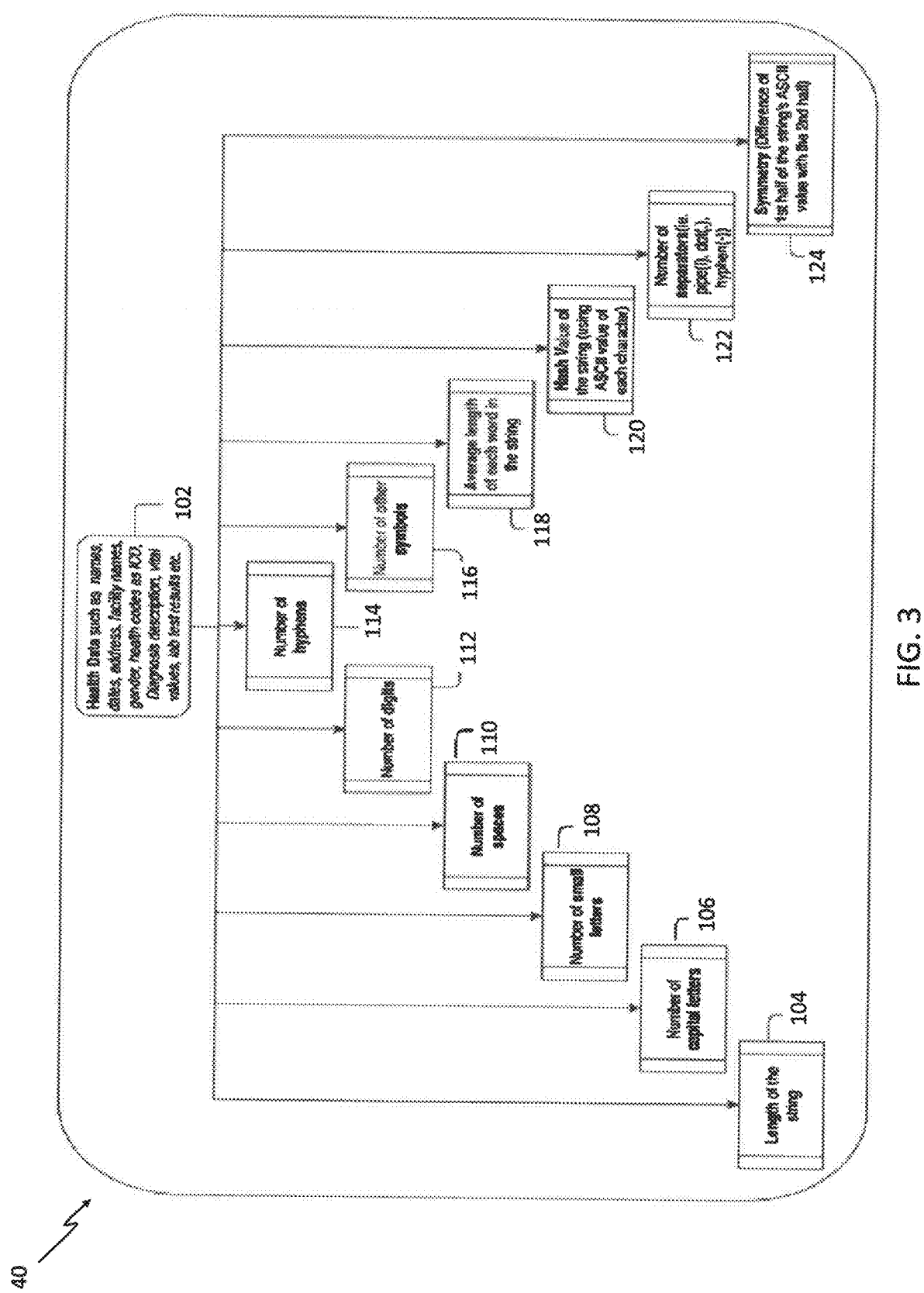
FIG. 3 is a diagrammatic illustration of extracted features from data elements of an XML format file, used with the system for the extraction of relevant data elements from an electronic file for conversion to a tabular format, in accordance with the first exemplary embodiment of the present disclosure.

FIG. 3 is a diagrammatic illustration of extracted features from data elements 36 of an XML format file, used with the system for the extraction of relevant data elements from an electronic file for conversion to a tabular format 10, in accordance with the first exemplary embodiment of the present disclosure. With reference to FIGS. 1-3 together, FIG. 3 provides a diagrammatical understanding of how the system 10 extracts features from the data elements 36 or other parts of the XML file 30, per block 40 of FIG. 1. For example, FIGS. 2 and 3 illustrate the various features which may be extracted from the textual elements of each data element 36, and/or attributes 38, or a string (a sequence of characters) thereof, to classify the underlying data between the various columns headers which are used as the target variables. The feature extraction process from each of these textual elements include various techniques for extracting data from the data element 36 and/or attributes 38. As an example, these textual elements are identified as "Health Data" at block 102 and include items such as patient names, dates, or addresses, facility names, gender, health codes as ICD, diagnosis, descriptions, vital values, lab test results, or other information. The features extracted, which may be used, include a length of the string 104, counts for uppercase letters 106, counts for lowercase letters 108, number of spaces 110, number of digits 112, number of hyphens 114, the number of symbols or non-alpha numeric characters other than a space 116, average length of each word in a string 118, a hash value calculated using the American Standard Code for Information Interchange (ASCII) value of each character 120, number of grammatical separators, including forward and backward slashes, pipe operator, hyphens, dashes, periods and dots, and less than and greater than symbols 122, and the symmetry value calculated using the ASCII value of each character, e.g., the difference of the first half of the string's ASCII value with the second half 124. These features may be used in the order listed herein or in another order, such as one which increases the efficiency or accuracy of the extraction process. Other extraction techniques may also be employed.

The features extracted are used to train the machine learning model. For example, in FIG. 3, the features extracted can be used to train the machine learning model to build a classifier, such as the demographics model, whose possible classes can be patient name, street address, city, state, postal code, country, email ID, telephone, gender, date of birth, marital status, race, ethnicity, and/or language spoken. Since the information for both the patient and the provider is contained within the "recordTarget" loop, as shown in FIG. 2, an XML document such as the C-CDA being semi-structured can aid in identifying the exact column to which the data element 36 belongs, in part, due to the looping nature of the XML format. For example, the patient's name and the provider's name will be recognized by the machine learning model as an entity that belongs to the column 'name'. However, the loop header "<patient" in line-14 and "<providerOrganization" in line-33 help to identify the context of the data element 36, e.g., whether it corresponds to the patient's name or the provider's name. Accordingly, the use of the machine learning model with the processing techniques described herein allow for the data elements in the unstructured or semi-structured format of the XML document to be classified, such that it can be converted into a data format which can be efficiently and accurately ingested into a tabular system widely used in the IT industry.

Figure 4:
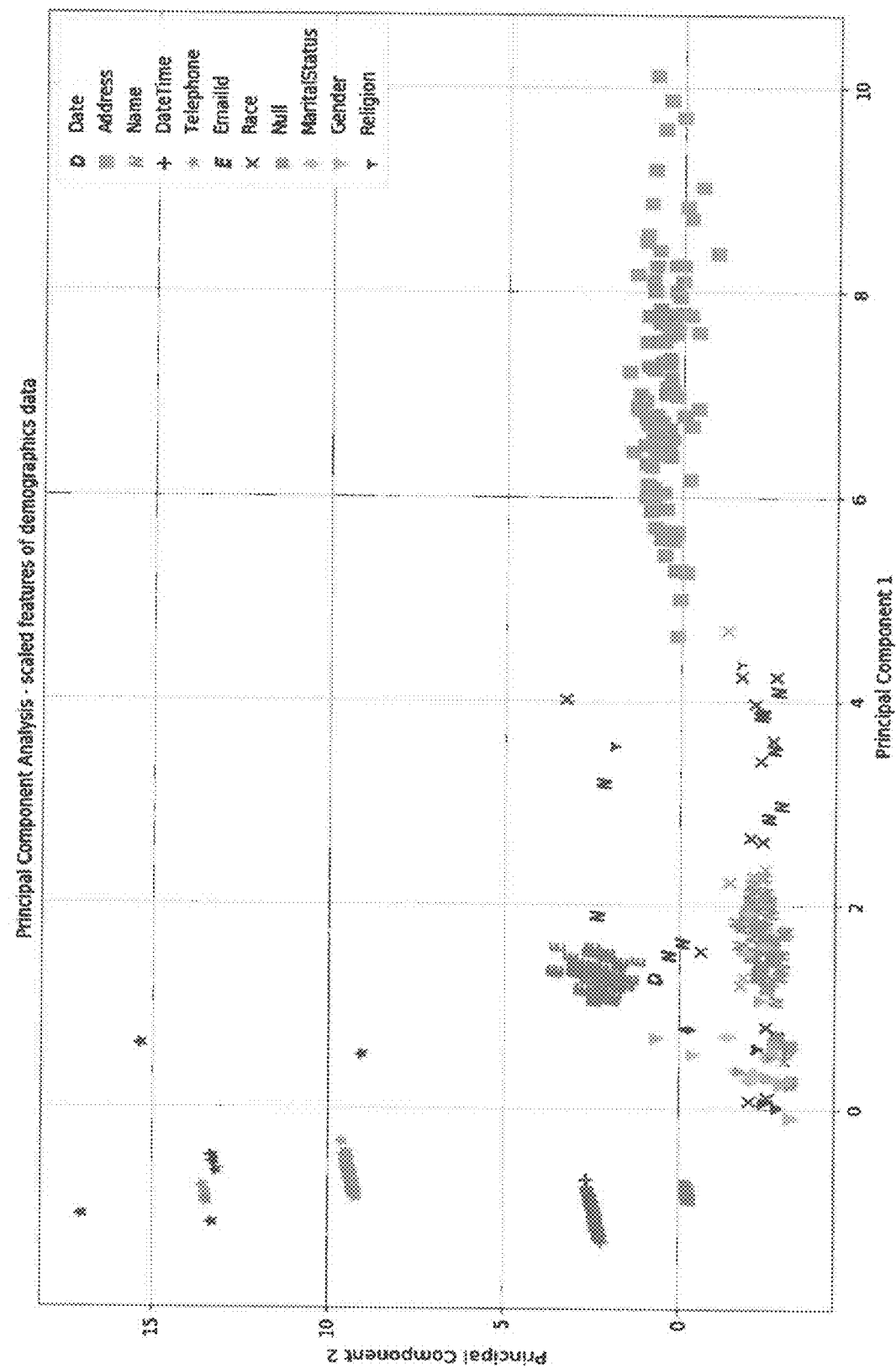
FIG. 4 is a graphical image of principal component analysis of extracted features from data elements of an XML format file, used with the system for the extraction of relevant data elements from an electronic file for conversion to a tabular format, in accordance with the first exemplary embodiment of the present disclosure.
Figure 5:
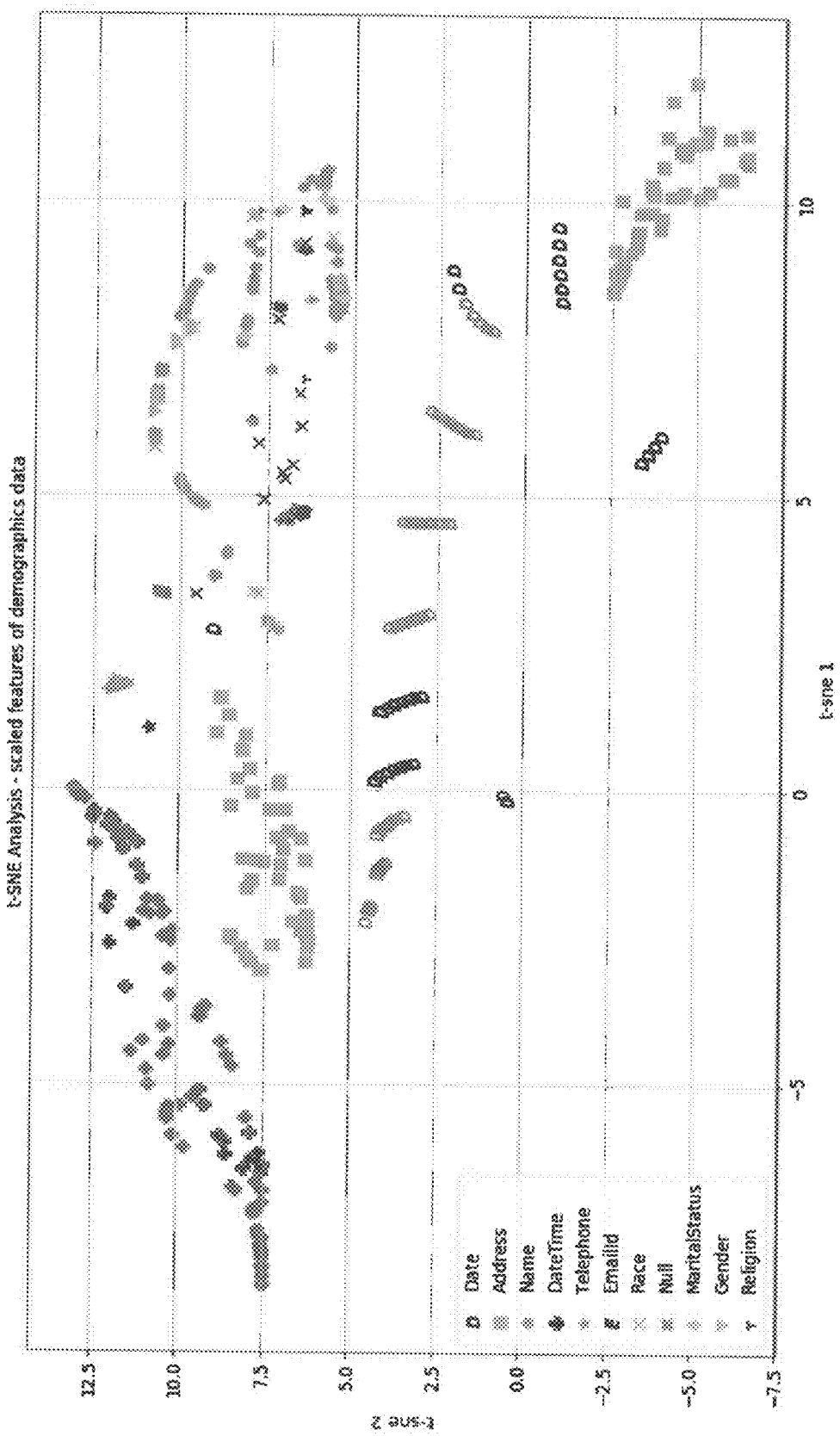
FIG. 5 is a graphical image of t-SNE analysis of extracted features from data elements of an XML format file, used with the system for the extraction of relevant data elements from an electronic file for conversion to a tabular format, in accordance with the first exemplary embodiment of the present disclosure.

FIGS. 4-5 illustrate an example of the methodology described relative to FIGS. 1-3, and in particular, the data element classification or segregation of block 60 in FIG. 1. FIG. 4 is a graphical image of principal component analysis of extracted features from data elements of an XML format file and FIG. 5 is a graphical image of t-SNE analysis of extracted features from data elements of an XML format file, both used with the system for the extraction of relevant data elements from an electronic file for conversion to a tabular format, in accordance with the first exemplary embodiment of the present disclosure. In particular, FIG. 4 illustrates the principal component analysis of the scaled values of the extracted features for the demographic data shown in FIG. 2, whereas FIG. 5 shows the t-SNE analysis of the scaled values of these extracted features for the demographic data. The scaling is done by using a scaler formula which includes subtracting each value in a feature column with its mean, and then dividing it by its standard deviation. As shown in FIG. 4, a clear distinction can be seen between the data element classes which contain only numeric characters or digits, such as the date and date time, or that contain only alphabet characters, such as names, religion, gender, and race. In contrast, classes that include both alphabet characters and numerical characters fall between, for example, the addresses. The t-SNE plot of FIG. 5 uses the features extracted and described in FIG. 4 and further shows the proof that the data classification is successful, as indicated by the tight groupings of each class on the plot.

Referring back to FIGS. 1-3, once the features of the data elements 36 and/or attributes 38 have successfully built a model to classify or segregate the data elements 36, a configuration file is generated, per block 70 of FIG. 1. The configuration file may be a JavaScript Object Notation (JSON) document, which is a lightweight data-interchange format that is easy for humans to read and write, but is also easy for machines to parse and generate. The configuration file contains the mapping of the column headers in the data structures to the XML XPath of the data elements 36 recognized. It is noted that the configuration file having the JSON format may effectively have the structure of a dictionary which contains the key value pair, as shown at 72. Here, the key may be the column header name from a data-lake schema and the value may be the XPath. As an example, the XPath for the first name of the patient may be as follows: first-name:recordTarget/patientRole/patient/given. The location of the first name was found using the machine learning model and it was flagged as first name of the patient, so a key-value pair is used to show this relationship. Similarly, the rest of the columns may be populated as a key value pair relations.

The configuration file may then be output from the computing device 20, such as through a network connection 22, where the configuration file can be used to parse the XML file or consumed, per block 80. In one example, the configuration file may be used to parse the XML file within the computing device 20, but it may be common for it to be parsed in another, separate computer or a plurality of parallel-operating computing devices. This separate computing system or systems may be used to extract the data elements 36 with the help of the underlying XML file 30 and the key-value pair of the configuration file 72, such that the XML file 30 can ultimately be output as a tabular representation, as shown at block 90. For example, a computer system at an IT data facility or elsewhere may ingest the configuration file and document and parse the C-CDA file to extract the data elements from the XML file to the tabular format. Once in the tabular format, the existing computing architecture and processing of the IT industry performs data analytics on the healthcare data efficiently and accurately, thereby improving the state of healthcare analytics.

It is noted that the process of parsing the XML file using the configuration file may be parallelized to attain maximum efficiency in aggregating the data elements 36 from the C-CDA document and improve the speed of the overall processing. Due to the volume of data and data elements in healthcare data, the use of parallelized processing may greatly improve efficiency in conversion of the health data to tabular format. Additionally, to ensure greater accuracy and data analysis, the methodology of this disclosure may exploit the capability of a computerized machine to go through each and every content of the clinical document as though mimicking the process of a human reading each document. For a human being this would be tedious, impractical, and very time consuming. Even for a high-end computer with high processing specs, it may take a considerable amount of time. A parallel programming approach which distributes the workload to several processors may be used to achieve the desired efficiency while maintaining the desired accuracy.

It is further noted that another advantage of the system 10 is that the machine learning model used may increase the accuracy of the data processing, since with less human intervention, the chances of making errors decreases significantly. The machine learning model is highly successful at finding all important data points, including those which may be scattered in the clinical document. Moreover, with no human intervention, the system 10 also ensures no patient health information (PHI) is leaked or read by any unauthorized entity in the organization while parsing the raw data, which is a strict requirement of HIPAA laws.

Figure 6:
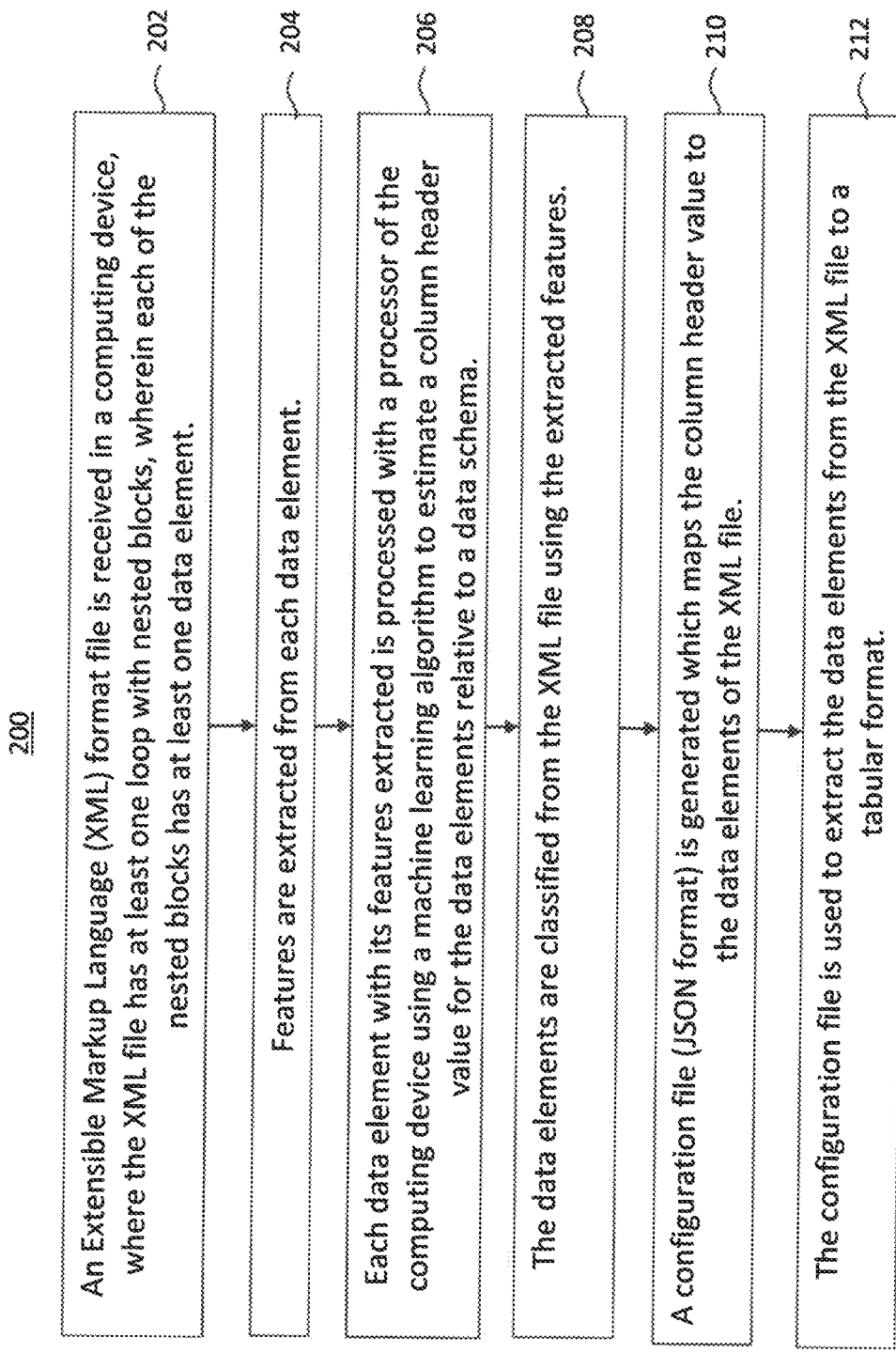
FIG. 6 is a flowchart illustrating a method for extracting relevant data elements from an electronic file for conversion to tabular format, in accordance with the first exemplary embodiment of the present disclosure.

FIG. 6 is a flowchart 200 illustrating a method for extracting relevant data elements from an electronic file for conversion to tabular format, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, an Extensible Markup Language (XML) format file is received in a computing device, where the XML file having at least one loop with nested blocks, wherein each of the nested blocks has at least one data element. Features are extracted from each data element of the XML file (block 204). The extracted features are processed with a processor of the computing device using a machine learning algorithm to estimate a column header value for the data elements relative to a data schema (block 206). The data elements are classified from the XML file using the extracted features (block 208). A configuration file, in JSON format, is generated which maps the column header value to the data elements of the XML file (block 210). The configuration file is used to extract or convert the data elements from the XML file to a tabular format (212). The method may further include any number of additional steps, variations, or functions, including any disclosed relative to FIGS. 1-5, all of which are considered within the scope of the present disclosure.

With implementation of the system and methods described herein, automated data extraction from unstructured or semi-structure clinical documents will drastically aid in improving the interface between the health industry and the IT industry by bringing the health data into the existing IT processing infrastructure faster, safer and more efficiently. The ability of the computers utilizing machine learning models to analyze each and every element in these clinical documents can decrease the average time spent in processing a clinical document from minutes (or longer) to seconds. The system and methods described herein can efficiently provide the health data to the data analytics teams of the IT organizations in a quick and efficient manner. In turn, this will help in developing insights and interventions for the patients by the health providers in the least possible time, which ultimately will improve and save lives.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A computer-implemented method for extracting relevant data elements from an electronic file for conversion to tabular format, the method comprising:

receiving, in a computing device, an Extensible Markup Language (XML) format file, the XML file having at least one loop with nested blocks, wherein each of the nested blocks has at least one data element, the at least one data element having an unstructured or semi-structured format;

extracting features from the data elements;

processing, with a processor of the computing device, the extracted features using a machine learning algorithm to estimate a column header value for the data elements relative to a data schema;

classifying, by the processor, the data elements from the XML file using the extracted features;

generating, by the processor, a configuration file which maps the column header value to the data elements of the XML file;

parsing the XML file using the configuration file to extract unstructured or semi-structured alphanumeric data values of the data elements from the XML file and convert the data elements to a structured tabular format; and ingesting the structured tabular format of the data elements into a data analytics processing system.

2. The method of claim 1, wherein the file having the XML format further comprises a Consolidated Clinical Document Architecture (C-CDA) file.

3. The method of claim 1, further comprising extracting features from at least one attribute describing the data element.

4. The method of claim 1, wherein the extracted features from the data elements further comprise at least one of: a length of a string, a number of capital letters, a number of lowercase letters, a number of spaces, a number of digits, a number of hyphens, a number of symbols, an average length of each word in the string, a hash value of the string, a number of grammatical separators, or a symmetry of the string.

5. The method of claim 4, wherein the hash value of the string and the symmetry of the string are calculated using an American Standard Code for Information Interchange (ASCII) value of each character within the string.

6. The method of claim 1, wherein the configuration file has a key value pair, where the key is the column header value name from a data-lake schema and the value is an XPath to the data element of the XML file.

7. The method of claim 1, further comprising outputting the configuration file to a separate computing device prior to parsing the XML file using the configuration file.

8. The method of claim 1, wherein parsing XML file using the configuration file to convert the data elements from the XML file to the tabular format is implemented simultaneously in parallel computing processors.

9. A computer-implemented system for the extraction of relevant data elements from an electronic file for conversion to a tabular format, the system comprising:

a computing device receiving an Extensible Markup Language (XML) format file, the XML file having at least one loop with nested blocks, wherein each of the nested blocks has at least one data element, the at least one data element having an unstructured or semi-structured format;

a processor of the computing device executing instructions for:

extracting features from the data elements of an XML file;

processing the extracted features using a machine learning algorithm to estimate a column header value for the data elements relative to a data schema;

segregating the data elements from the XML file using the extracted features; and generating a configuration file which maps the column header value to the data elements of the XML file;

parsing the XML file using the configuration file to extract unstructured or semi-structured alphanumeric data values of the data elements from the XML file and convert the data elements to a structured tabular format; and ingesting the structured tabular format of the data elements into a data analytics processing system.

10. The system of claim 9, wherein the file having the XML format further comprises a Consolidated Clinical Document Architecture (C-CDA) file.

11. The system of claim 9, further comprising extracting features from at least one attribute describing the data element.

12. The system of claim 9, wherein the extracted features from the data elements further comprise at least one of: a length of a string, a number of capital letters, a number of lowercase letters, a number of spaces, a number of digits, a number of hyphens, a number of symbols, an average length of each word in the string, a hash value of the string, a number of grammatical separators, or a symmetry of the string.

13. The system of claim 12, wherein the hash value of the string and the symmetry of the string are calculated using an American Standard Code for Information Interchange (ASCII) value of each character within the string.

14. The system of claim 9, wherein the configuration file has a key value pair, where the key is the column header value name from a data-lake schema and the value is an XPath to the data element of the XML file.

15. The system of claim 9, further comprising outputting the configuration file to at least one separate computing device prior to parsing the XML file using the configuration file.

16. The system of claim 9, wherein parsing the XML file using the configuration file to convert the data elements from the XML file to the tabular format is implemented simultaneously in parallel computing processors.

17. A computer-implemented system for extracting relevant health information from a clinical document in an Extensible Markup Language (XML) format for conversion to a tabular format, the system comprising:

a first computing device receiving the clinical document, wherein the clinical document has a plurality of loops with a plurality of attributes describing data elements, the plurality of data elements having an unstructured or semi-structured format, wherein the plurality of data elements correspond to health information within the clinical document;

a processor of the first computing device executing instructions for:
extracting features from at least one of the plurality of attributes or the data elements of a clinical document using textual analysis;

processing the extracted features using a machine learning algorithm to estimate a column header value for the data elements relative to a predefined data schema;

segregating the data elements from the clinical document using the extracted features; and generating a configuration file which maps the column header value to the data elements of the clinical document using a key-value pair, where a key of the key-value pair provides a column header value name from a data-lake schema and a value from the key-value pair provides an XPath of the clinical document;

at least one second computing device in communication with the first computing device, wherein, at the at least one second computing device, the configuration file is used to parse the data elements from the clinical document to a tabular format by extracting unstructured or semi-structured alphanumeric data values of the data elements from the clinical document and converting the data elements to a structured tabular format; and a data analytics processing system ingesting the structured tabular format of the data elements.

18. The system of claim 17, wherein the at least one second computing device further comprises a plurality of second computing devices operating simultaneously, wherein using the plurality of second computing devices in parallel, the configuration file is used to extract the data elements from the clinical document to the tabular format.

19. The system of claim 17, wherein the extracted features from the data elements further comprise at least one of: a length of a string, a number of capital letters, a number of lowercase letters, a number of spaces, a number of digits, a number of hyphens, a number of symbols, an average length of each word in the string, a hash value of the string, a number of grammatical separators, or a symmetry of the string.

20. The system of claim 19, wherein the hash value of the string and the symmetry of the string are calculated using an American Standard Code for Information Interchange (ASCII) value of each character within the string.

* * * * *